United States Patent [19]
Cohen

[11] Patent Number: 4,855,305
[45] Date of Patent: Aug. 8, 1989

[54] COMPOSITIONS AND METHODS OF EFFECTING CONTRACEPTION UTILIZING MELATONIN

[75] Inventor: Michael Cohen, Wassenaar, Netherlands

[73] Assignee: Applied Medical Research, Washington, D.C.

[21] Appl. No.: 29,229

[22] Filed: Mar. 23, 1987

[51] Int. Cl.$^4$ ............... A61K 31/56; A61K 31/40; A61K 31/405
[52] U.S. Cl. .................... 514/171; 514/415; 514/419
[58] Field of Search ............ 514/415, 419, 171

[56] References Cited

U.S. PATENT DOCUMENTS

| | | | |
|---|---|---|---|
| 4,087,444 | 5/1978 | Flaugh et al. | 260/326.13 |
| 4,390,531 | 6/1983 | Edgren | 514/170 |
| 4,425,339 | 1/1984 | Pitchford | 514/170 |
| 4,614,807 | 9/1986 | Flaugh | 548/507 |

OTHER PUBLICATIONS

Nordlund et al., *J. Clin. Endocrin. Metab.* 45: 768–770 (1977).
Weinberg et al., *J. Clin. Endocrin. Metab.* 51: 161–162 (1980).
Wright et al., *Clinical Endocrinology* 24: 375–382 (1986).
Cardinelli, *Endocrine Reviews* 2: 237–346 (1981).
Reiter, *J. Obstet and Gynaecol.* 6 (Supp. 2): 577–581 (1986).
William, *Br. Vet. J.* 140(4): 407–8 (1984).
Arendt et al., *J. Endocrinol.* 97:395–400 (1983).
Kennaway et al., *Endocrinology* 110(5): 1766–72 (1982).
Reiter, in Slott et al., Ed. *Brain Endocrine Interaction III. Neural Hormones and Reproduction,* Basel Karger (1978).
Berga, et al., *J. Clin. Endocrinol. Metabl.*, 242–244 (1988).
Webley, et al., *J. Clin. Endocrinol. Metab.* 63:323–328 (1986).
Carr, et al., *J. Clin. Endocrinol. Metab.* 53: 224–225 (1981).
Tamarkin, et al., *Endocrinology* 99: 1534–1541 (1976).
Bittman, *Science* 1978 202 (4368) 648–50 (1978).
Guidelines for the Toxicological and Clinical Assessment and Post Registration Surveillance of Sterional Contraceptive Drugs by the World Health Organization (1987).
Kirton, in *Animal Models for Predicting Toxicity of Fertility Control Agents,* Raven Press, Serjo et al. ED. 455–460 (1980).
Bosu et al., *Contraception* 13: 677–684 (1976).
Perlow et al., *Brain Res., 182:211–216 (1980).*
Fideleff et al., *J. Clin. Endocrin. Metab.,* 42(6): 1014 (1976).
Brzezinski et al., *J. Clin. Endocrin. Metab.* 66:(5):891 (1987).
Reiter et al., *J. Neural Trans.* Supp. 13:209 (1978).
Walker et al., *Endocrinology* 114($):1074 (1984).
Kumar et al., "Nasal Sprays for Controlling Ovulation in Rehsus Monkeys".
Kumar et al., *Nature* 270:532 (1977).
Reiter, Journal of Obstetrics and Gynecology (1986), S77–81.
Kumar, et al. Satellite Symp. 7th Congr. Int. Primatol Soc. Bangalore 1979, pp. 169–175.
Ying et al., Endocrinology 92:333, 1973.
Flaugh, et al., Journal of Medicinal Chem, 1979, vol. 22, No. 1.
Chu et al., Endocrinology, 75: 238, 1964.
Tamarkin, et al., Science, vol. 227, Jan. 1985, 714–720.

(List continued on next page.)

*Primary Examiner*—Douglas W. Robinson
*Assistant Examiner*—Joseph A. Lipovsky
*Attorney, Agent, or Firm*—Bernard, Rothwell & Brown

[57] ABSTRACT

A method of effecting contraception in human females comprises administering an ovulation-inhibiting amount of melatonin. Optionally, the melatonin is administered in combination with a progestogen and/or an estrogen. The administration of melatonin also provides a method of preventing breast cancer in women.

36 Claims, 4 Drawing Sheets

OTHER PUBLICATIONS

Espey, et al., Fertil Steril 38 (2) 1982, 238–247.
Sharpe et al., Theriogenology 26(5), 1986, 621–630.
Nowak et al., J. Reprod Fertil 74(1), 1985, 287–294.
Kennaway, et al., J. Reprod Fertil 70(1), 1984, 39–46.
Chemineau, et al., J. Reprod. Fertil 78(2), 1986, 497–504.
Nett et al., Theriogenology 17(6), 1982, 645–654.
Fiske et al., Endocrinology, vol. 114, No. 2, 1984, pp. 407–410.
Webley et al., J. Reprod. Fert. (1986) 78, 711–717.
Webley et al., J. Clin. Endocrinol. Metab., 63(2), 323–8.
Tamarkin, Science, vol. 26, 28 May 1982, 1003–1005.
Tamarkin et al., Cancer Research, vol. 41 4432–4436, (1981), 4432–4435.
Danforth et al., J. Clin. Oncol 3 (7), 1985, 941–948.
Heywood, in *Animal Models in Human Reproduction*, Raven Press, M. Serjo et al., Ed. 433–442 (1980).

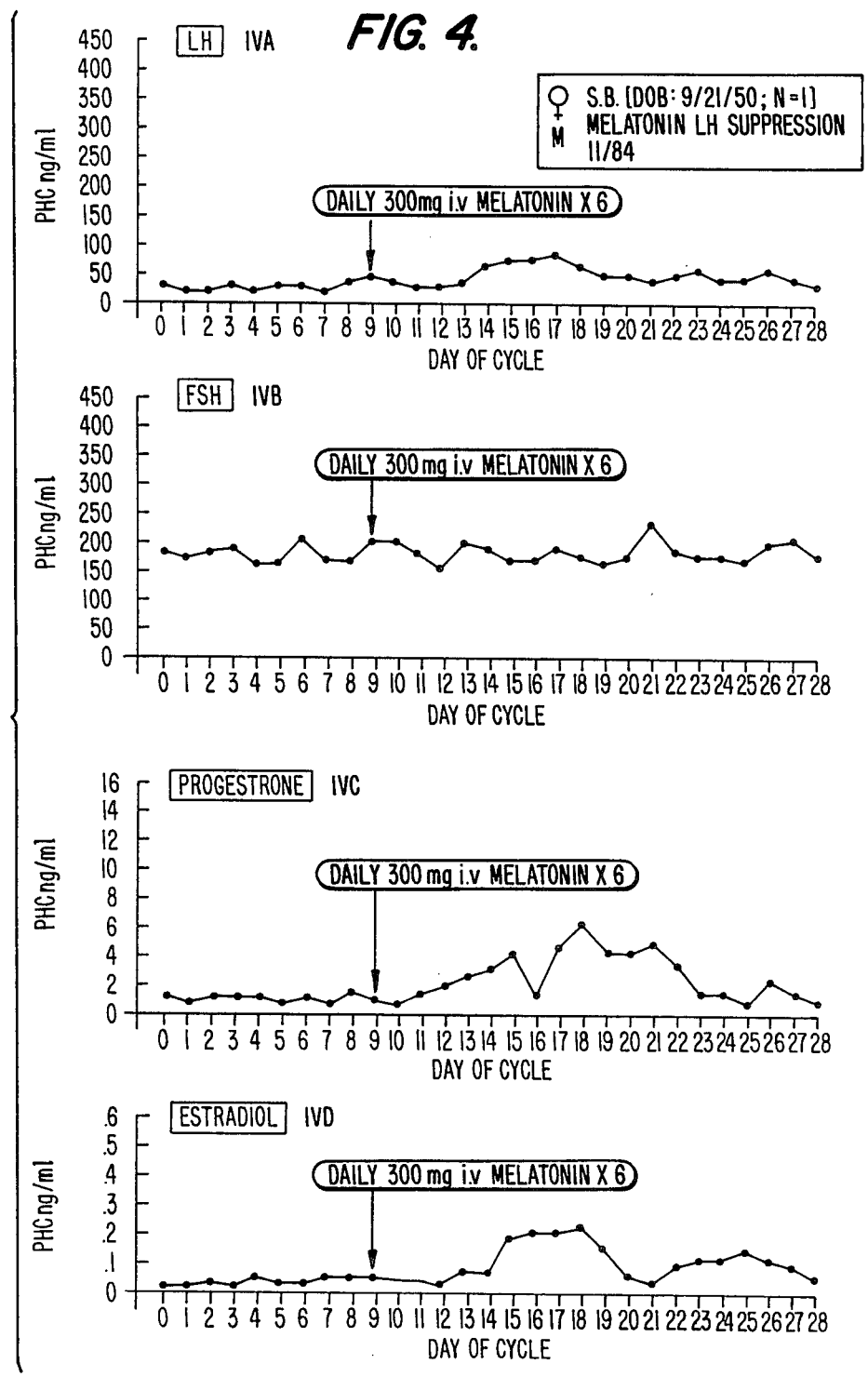

COMPOSITIONS AND METHODS OF EFFECTING CONTRACEPTION UTILIZING MELATONIN

FIELD OF THE INVENTION

This invention relates to a method of inhibiting ovulation in human females. More particularly, the invention relates to a method of inhibiting ovulation by administering an ovulation-inhibiting amount of melatonin. Optionally, the melatonin is administered in combination with a progestational and/or estrogenic agent.

BACKGROUND OF THE INVENTION

Research and development in the field of contraception in humans has been in the areas of physical and chemical barriers to sperm transport, such as vaginal foams, diaphragms, intrauterine devices, and condoms, and in the area of oral contraceptives containing one or more steroid hormones. Oral contraceptives have been developed which are highly effective in preventing contraception, and today more than fifty million women around the world use oral contraceptives. Typically, the oral contraceptives take the form of a combination of an estrogen and a progestogen (also known as progestin). In some of these regimens, known as combination regimens, a consistent dose of an estrogen and a progestogen is administered daily throughout the period of administration. In other regimens, referred to as sequential regimens, the amount of estrogen or progestogen or both is increased or decreased during the menstrual cycle. Some sequential regimens provide two-stage or bi-phasic control. (See, for example, U.S. Pat. No. 3,969,502). Others provide a three-stage or tri-phasic combination of components. (See, for example, U.S. Pat. Nos. 4,628,051; 4,390,531.) A third type of regimen also is known in which one or more progestogens is administered daily throughout the menstrual cycle.

The hormones in oral contraceptives act both within the central nervous system and in tissues of the urogenital tract to inhibit reproductive function. The principal sites of action are the hypothalamus and pituitary to prevent the midcycle surge of luteinizing hormone (LH) and hence to prevent ovulation. The basal concentrations of LH and follicle-stimulating hormone (FSH) and plasma levels of estradiol and progestrone are suppresed in users of oral contraceptives. In essence, these contraceptives work by causing changes in hormone levels that imitate those caused by pregnancy. This effect is dose dependent. These conventional oral contraceptives are administered for a minimum of 21 days of a woman's cycle, and in some instances for the entire 28-30 days of the cycle.

Oral contraceptives also exert a direct effect on the urogenital tract. They alter the structure and physical-chemical composition of the endometrium and the consistency of the cervical mucous, thus altering the uterine capacity for the ovum to implant.

Oral contaceptives have been shown to provide benefits other than the prevention of pregnancy. Compared to non-users, women who take oral contraceptives have been shown to have a lower risk of pelvic inflammatory disease (PID), ectopic pregnancy, endometrial cancer, and benign breast disease. Most significantly, the current combination-type contraceptives also are responsible for reducing the incidence of ovarian cancer. Oral contraceptives also can provide relief from common menstrual disorders, including irregular menses, premenstrual tension, excess blood loss and cramps.

Use of conventional oral contraceptives, however, also is attended by certain risks. These risks, which include a greater chance of suffering from venous thromboembolism, ischemic heart disease, cerebrovascular disease and hypertension, are believed to be largely due to the estrogen component (typically ethinyl estradiol or menstranol) in the contraceptives. The risk of suffering from any of these conditions has been found to be confined primarily to women over age 35, especially to women over age 35 who smoke. Women who take estrogen also may suffer other negative side effects, including gastrointestinal disturbances, nausea and weight gain.

In an effort to avoid the negative side effects or possible side effects associated with oral contraceptives containing estrogen, oral contraceptives containing only one or more progestogens as the active component have been developed. These contraceptives, however, generally have been found to be less effective than those containing both an estrogen and a progestogen. One common side effect suffered by women who take oral contraceptives which contain only progestogen is breakthrough bleeding during the menstrual cycle.

In view of the drawbacks and negative side effects of conventional oral contraceptives, new contraceptives are sought. Accordingly, it is an object of the present invention to provide a contraceptive method which is highly effective and provides the benefits and avoids the adverse effects associated with contraceptives currently used. It also is an object of this invention to provide a method of reducing the incidence of breast cancer in women.

SUMMARY OF THE INVENTION

In accordance with the present invention there is disclosed a method for effecting contraception in human females of child-bearing age by administering melatonin in dosages effective to prevent ovulation. Optionally, the melatonin is administered in combination with a progestogen and/or an estrogen. In a preferred embodiment, the contraceptives of this invention are administered in oral dosage form. In accordance with the present invention there also is disclosed a method for preventing breast cancer in human females by administering effective doses of melatonin.

DETAILED DESCRIPTION OF THE INVENTION

Figure 1:
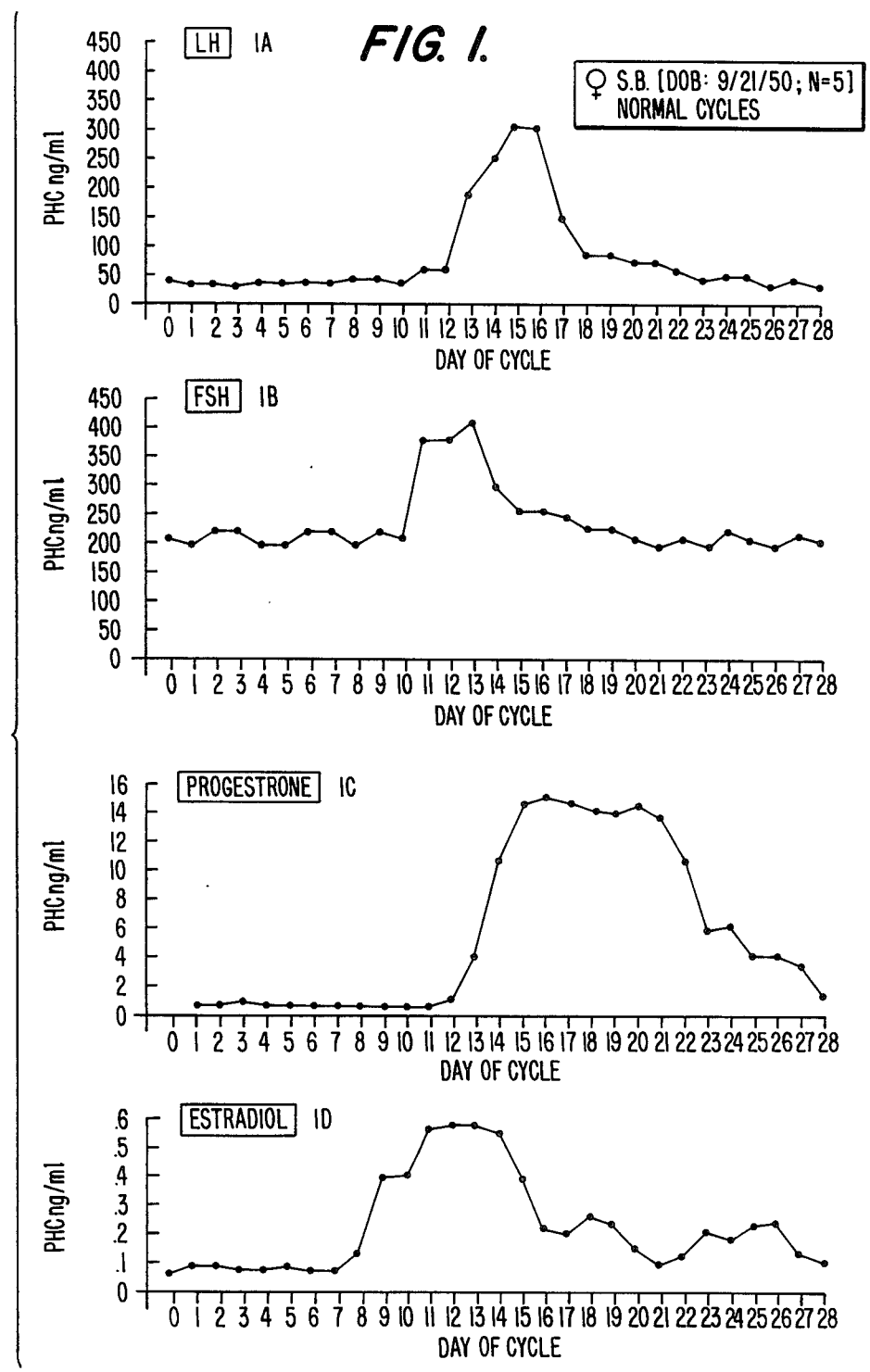
Figure 2:
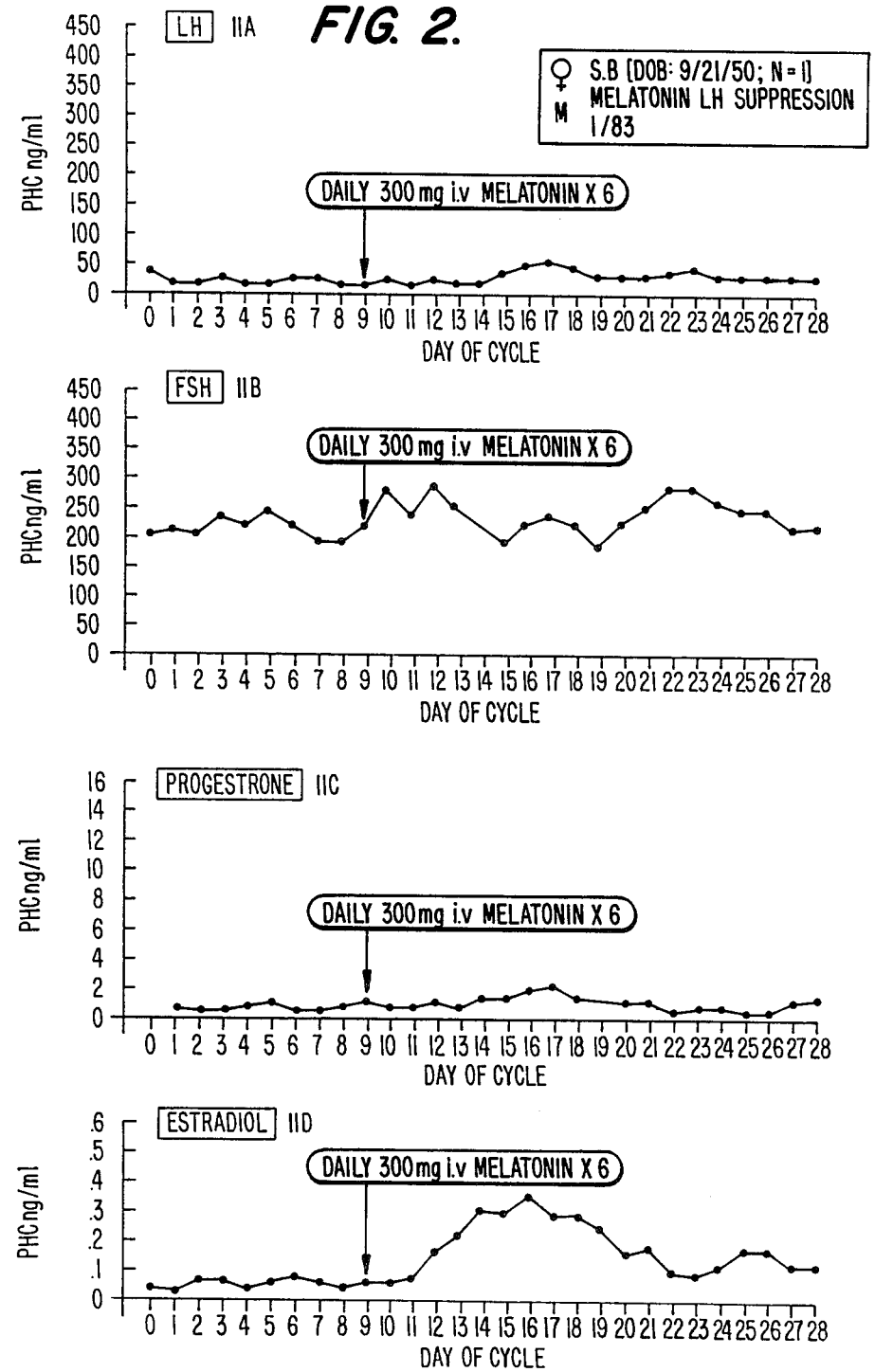
Figure 3:
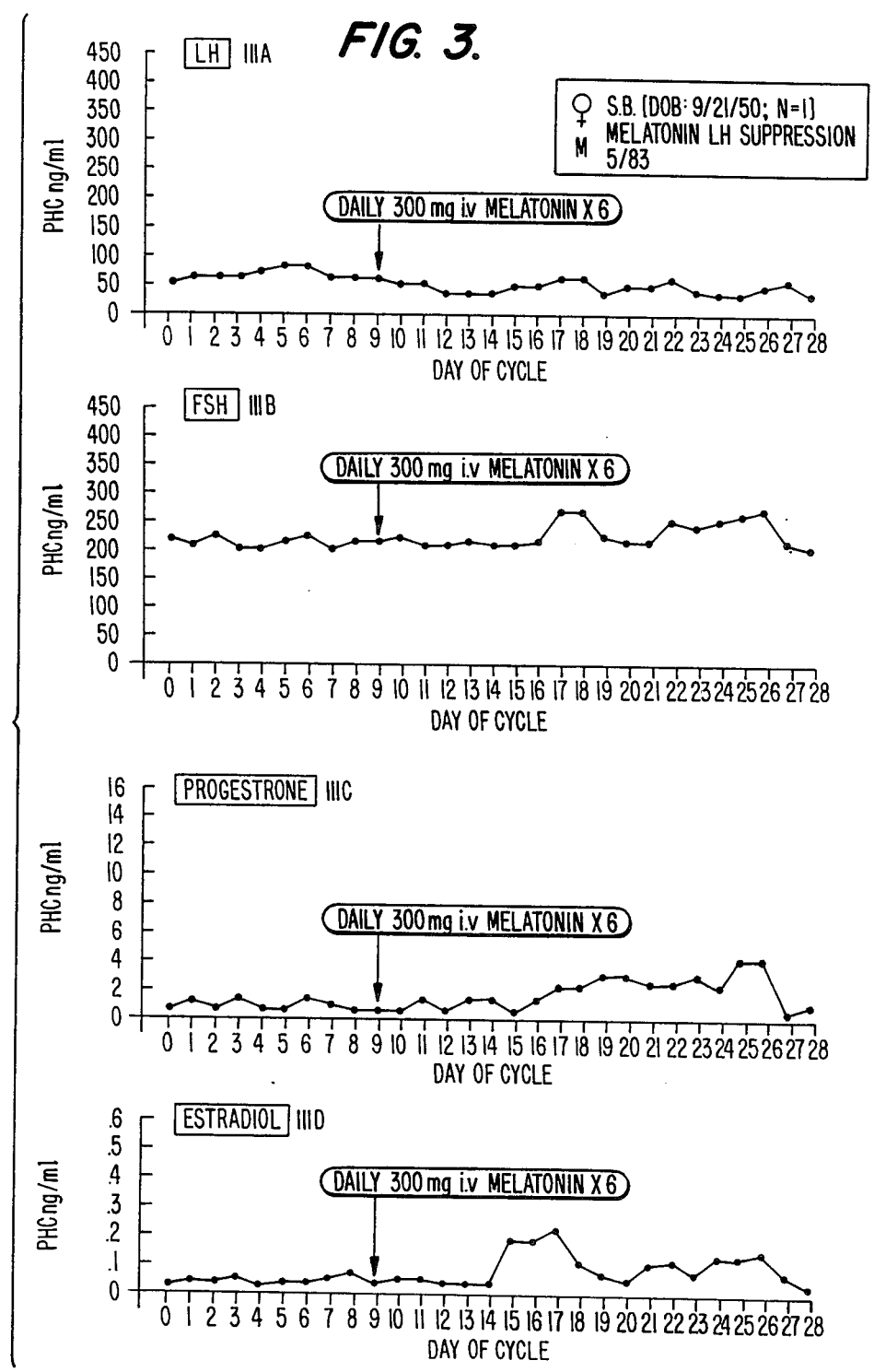

Melatonin (N-acetyl-5-methoxytryptamine) is a hormone synthesized and secreted by the pineal gland. The exact role of the hormone has not yet been determined. Studies have shown that the injection of melatonin into Syrian golden hamsters at certain specific times of the day has had an inhibitory effect on the development of the gonads, the weight of the testes in males and on ovulation in females. Female rats injected with melatonin at certain times of the day also showed an inhibition of ovulation. Melatonin thus has been shown to have a primary inhibitory effect on the gonads in various rodent species. A similar effect, however, has not been shown in other mammalian species injected with melatonin. Specifically, the adminstration of melatonin to sheep (Kenneway, D. J. et al., *J. Reproductive Fertility* 73:859[1985]) and to primates (Reppert, S. M., et al., *Endocrin.* 104:295[1979]) did not result in a direct alteration of their reproductive physiology. Exogenous melatonin administration in humans has been studied in conjunction with a hypothesis that an abnormal melatonin rhythm is associated with endogenous depression and for pharmokinetic purposes (Waldhauser, F., *Neuroendocrinology* 39:307, 313 [1984]) and in connection with sleep-wake rhythms and the phenomenon of "jet-lag" following airplane trips associated with a change in time zones.

The present invention is based on the discovery that pharmacological doses of melatonin administered daily to a female selectively suppresses the normal mid-menstrual cycle surge in leutinizing hormone sufficient to prevent ovulation. The present invention is directed to a method of effecting contraception in a human female of child-bearing years by daily administering to the female melatonin in dosages effective to prevent ovulation by suppressing the surge in leutinizing hormone which occurs prior to, and is required for, ovulation.

The present invention also is directed to a method of preventing the induction of breast cancer in women. It has been discovered that pharmacological administration of melatonin prevents 7,12-dimethylbenzanthracene (DMBA) induced adeno-carcinoma in various rodent species. It also has been discovered that women with estrogen receptor positive breast cancer have a decreased nocturnal melatonin concentration (Tamarkin, D. et al., *Science* 216:1003–1005 (1982)). Although not wishing to be bound by theory, it is believed that the administration of pharmacological doses of melatonin will prevent the buildup of cells in the breast tissue that can occur during the menstrual cycle. It is theorized that this build-up of cells, if it continues over a long period of time, can result in the development of a tumor, and that the administration of melatonin will stabilize cell growth such that there are a balanced number of cells in the breast tissue in each reproductive cycle.

As used herein, the term melatonin also encompasses melatonin analogs which have an ovulation inhibiting effect when administered to human females. Such melatonin analogs include 6-fluoromelatonin, 5-hydroxytryptamine, 5-methoxyindole, and 5-methoxytryptamine. Other such melatonin analogs include those disclosed in U.S. Pat. Nos. 4,087,444 and 4,614,807, incorporated herein by reference.

The melatonin (or melatonin analog) is administered daily in dosages sufficient to suppress the user's normal surge in leutinizing hormone and thus prevent ovulation. Generally, the melatonin is administered in amounts ranging between about 2 mg and about 1000 mg per day per 70 kilograms body weight of the woman receiving the melatonin. Preferably about 30 mg to about 500 mg melatonin are administered daily.

The melatonin can be administered every day throughout a woman's cycle. It has been found, however, that administration of melatonin for only a 1 to about 7 day period in the cycle which immediately precedes the woman's normal day of ovulation is sufficient to achieve a contraceptive effect. Ovulation typically occurs on the fourteenth cycle day or alternatively between about the ninth and seventeenth day of a woman's cycle. This regimen is preferred for administering the melatonin. The type of regimen selected can affect the amount of melatonin administered daily. The amount provided in each daily dosage also can vary with the method of administration selected.

The melatonin can be administered to women either orally, parenterally or in the form of an implant. Administration is most convenient when the melatonin is in oral dosage form, such as capsules, tablets, suspensions or solutions. Capsules or tablets are preferred. Capsules can be prepared by mixing the compound with a pharmaceutically-acceptable excipient and then filling gelatin capsules with the mixture in accordance with conventional procedures. Alternatively, the melatonin can be mixed with one or more lubricants, such as stearic acid or magnesium stearate, flavor ameliorating agents, disintegrating elements, including potato starch and alginic acid, binders, such as gelatin and corn starch, and/or tablet bases including lactose, corn starch and sucrose, and then pressed into tablets.

As an alternative to oral administration, the melatonin can be administered parenterally or in the form of a solid implant. For parenteral administration, the melatonin is provided in injectable doses of a solution or suspension of the hormone in a physiologically acceptable diluent with a pharmaceutical carrier. The carrier can comprise water or an oil and optionally also can contain a surfactant or other pharmaceutically acceptable adjuvant. Suitable oils include those of animal, vegetable, petroleum or synthetic origin, including peanut, soybean, corn, sesame, castor and mineral oil. Preferred liquid carriers include water, saline, aqueous sugar solutions, and glycols such as propylene glycol or polyethylene glycol.

The melatonin also can be administered in the form of an implant, which is formulated such that it will provide a sustained release of the melatonin over time. To make the implant, the melatonin can be compressed into small cylinders and placed inside a physiologically acceptable shell material such as a biodegradable or porous polymer in accordance with conventional implant technology.

In a preferred embodiment of this invention, the melatonin is administered in combination with a progestogen. The progestogen is added to induce a cyclic bleeding resembling a cyclic menses bleeding and to provide the benefits currently associated with the administration of progestogens in conventional oral contraceptives. Any progestationally active compound is suitable for use as the progestogen component in the present invention. Suitable progestogens include progesterone and derivatives thereof. The presently preferred progestogen is norethindrone (i.e., 19-nor-17α-ethynyl-17β-hydroxy-4-androsten-3-one) and norgestrel (13β-ethyl-17α-ethynyl-17βhydroxygon-4-en-3-one). Other progestogens include the chlormadinone-acetate (6-chloro-17-hydroxy-pregna-4,6-diene-3,20-dione acetate), norethynodrel (17α-ethynyl-17-hydroxy-estr-5(10)-en), medroxyprogesterone acetate (17α-acetoxy-6α-methylpregn-4-ene-3,20-dione), megestrol acetate (17α-acetoxy-6-methyl-pregna-4,6-diene-3,20-dione), lynestrenol (17α-ethynyl-17β-hydroxy-estr-4-ene), quingestrone (3-cyclopentyloxy-pregna-3,5-diene-20-one), norethindrone acetate (17β-acetoxy-17α-ethynyl-estr-4-en-3-one), ethynodiol acetate (3β,17β-diacetoxy-17α-ethynylestr-4-ene), dimethisterone [17β-hydroxy-6α-methyl-17-(1-propynyl)-androst-4-en-3-one], and levonorgestrel.

A number of regimens are suitable for administering a combination of melatonin and a progestogen. For example, assuming a 28 day cycle, both the melatonin and progestogen can be administered for about 21 days, followed by adminstration of the melatonin without the progestogen for about 7 days. In a second regimen the melatonin and progestogen are administered for about 21 days, and then both are withheld for about 7 days.

In a third regimen, the melatonin is administered for about 5–14 days, followed by administration of the progestogen for about 7–14 days for a combined total of about 21 days. Neither the melatonin nor the progestogen is administered for the remaining 7 days of the cycle. A fourth regimen comprises administering a placebo for the first 5 days, then administering melatonin for about 3–7 days, followed by administration of the progestogen through the twenty-first day of the medication. Again, neither melatonin nor the progestogen is administered for the remaining 7 days of the cycle.

In another regimen, a progestogen is administered for about 21 days. Melatonin is administered in combination with the progestogen for about 1–7 days (preferably to about 3–5 days) at mid-cycle, just prior to the user's normal day of ovulation. At the end of about 21 days, the progestogen is withdrawn for about 7 days. As noted above, the conventional 21–28 daily dose progestogen-only contraceptives have not been very effective. The addition of melatonin overcomes the inefficacy of administering progestogen alone.

The progestogen component of these contraceptives generally is administered in the range of about 7.5 $\mu$g to about 2500 $\mu$g per day, preferably in the range of about 7.5 to about 600 $\mu$g per day. Most preferably, the progestogen is administered in the range of about 7.5 $\mu$g to about 250 $\mu$g per day. The actual amount of progestogen provided in each daily dosage will depend upon the particular progestogen chosen, its relative potency, and the method of administration selected. For example, a lesser quantity of a more potent progestogen may achieve the same results as a larger quantity of a less potent progestogen. As noted above, the amount of progestogen also can vary with the mode of administration, with lower doses typically needed for administration of an implant or intravenous injection than for oral administration.

In any of the suggested regimens set forth above, on those days in which both melatonin and a progestogen are administered, the two active components conveniently are combined and administered together, although they also ca be administered separately.

In an alternative embodiment of the present invention, a small amount of an estrogen can be added to any of the melatonin or melatonin-progestogen regimens set forth above. The estrogen can be added, if desired, to stabilize the melatonin by preventing any escape ovulation that might possibly occur if the melatonin is administered in the absence of an estrogen. Any conventional estrogen can be employed as a suitable component of the contraceptive compositons of the present invention. The presently preferred estrogens are ethinyl estradiol (i.e. 17$\alpha$-ethynyl-3,17$\beta$-dihydroxy-estra-1,3,5(10)-triene) and mestranol (17$\alpha$-ethynyl-17$\beta$-hydroxy-3-methoxy-estra-1,3,5(10)triene). Other suitable estrogens include estradiol (3,17$\beta$-dihydroxy-estra-1,3,5(10)-triene), estriol(3,-16$\alpha$,17$\beta$-trihydroxy-estra-1,3,5(10)-triene), estrone (3-hydroxy-estra-1,3,5(10)-triene-17-one), diethylstilbestrol, quinestradiol (3-cyclopentyloxy-16$\alpha$,17$\beta$-dihydroxy-estra-1,3,5-(10)-triene) and estrone sulfate. The estrogen can be administered daily throughout 21 days of the 28 day cycle in any of the regimens set forth above, but preferably it is administered only prior to the normal day of ovulation. The estrogen generally is administered in the range of about 2 $\mu$g to about 100 $\mu$g per day and preferably in the range of about 10 $\mu$g to about 50 $\mu$g per day. As with the progestogen, the actual amount of estrogen used in a daily dosage will depend upon the particular estrogen selected and its relative potency. Ethinyl estradiol, for example, has twice the biological potency as mestranol. Given the deleterious side effects of estrogen, desirably only the minimum amount of estrogen needed to stabilize the melatonin is used. The estrogen can be combined with the melatonin and/or progestogen in any of the regimens suggested above. In an alternative regimen, an estrogen is administered at the beginning of a woman's cycle for about 5–13 days, followed by the administration of melatonin for about 1–7 days (preferably for about 3–5 days) prior to her normal day of ovulation, then a progestogen is administered through about the twenty-first day of her medication.

In another embodiment of this invention, melatonin can be administered as a "morning after" pill, either by itself or in combination with an estrogen and or progestogen. In this embodiment, the melatonin is administered in daily doses of about 100 mg. to about 10,000 mg., preferably a dose of at least 2000 mg., over a 1–5 day post-coital period. If the melatonin is administered in combination with a progestogen and/or an estrogen, the progestogen preferably is administered in a daily amount ranging between about 10 mg and 20 mg, and the estrogen is administered in a daily amount ranging between about 2.5 and 25 mg.

In the preferred embodiment of this invention, the contraceptive compositions of this invention are administered in oral dosage form, preferably in the form of pills or capsules. The pills or capsules can be packaged in any manner suitable for proper delivery and use. Preferably, they are packaged in the form of a pharmaceutical kit or package in which the daily unit dosage forms are provided or arranged in a contiguous, sequential order which will enable the woman taking the pills to take the proper formulation at the appropriate time in her reproductive cycle. Suitable kits or packages include the conventional bubble plastic package containing individual bubbles for either 21 or 28 pills, depending upon the regimen selected, in a sheet of flexible plastic. The bubbles are sealed by a sheet of plastic which can break and release a pill when the bubble is pressed. On the first day of her medication, which is generally the first day after the cessation of bleeding from her last menstrual period the first pill in the sequence, whether it contains the contraceptive or a placebo, is removed from its individual slot and taken. The next pill in the sequence is taken the next day and so on thereafter until the dispenser is empty. A new dispenser is begun on day seven of her next cycle. Appropriate notations or instructions can be placed on the dispensing kit to guide or instruct the user in the proper use of the oral contraceptives.

As noted above, it also has been discovered that the administration of melatonin in the amounts of the regimens disclosed above can be effective in preventing breast cancer. This discovery provides an important benefit to human females of child-bearing age who take melatonin or the compositions of this invention containing melatonin as a contraceptive. In addition, melatonin and melatonin-containing compositions of this invention can be administered to post-menopausal women as a method of preventing breast cancer. The melatonin desirably is administered to post-menopausal women in daily doses of about 2 mg. to about 1000 mg., as discussed above. A progestogen and/or an estrogen can be combined with the melatonin and administered in the amounts and regimens set forth above to prevent the induction of breast cancer.

The present invention is further described and illustrated by the folowing examples, which are provided for informational purposes and are not to be construed as limiting.

EXAMPLE I

The contraceptive effectiveness of melatonin was studied in a patient, referred to herein by the initials S. B., born Sept. 21, 1950. In FIGS. IA, IB, IC and ID, respectively, are shown the concentration in her blood of leutinizing hormone (LH), follicle stimulating hormone (FSH), progestrone and estradiol for each day of her cycle, averaged over 5 consecutive cycles. As shown in the figures, this patient had a normal LH preovulatory surge and an FSH peak followed by a post-ovulatory progestrone rise. In the figures, the legend PHC stands for plasma hormone concentration.

For each of three cycles the patient was given intravenously 300 mg of melatonin in a physiological solution of glucose in saline from day 9 of her cycle for 6 consecutive days. FIGS. IIA, IIB, IIC and IID show the effects of the melatonin administration during the first cycle (January, 1983). The figures show an anovulatory cycle following the injections. FIGS. IIIA–IIID show the results of melatonin administration in the second cycle (May, 1983) and FIGS. IVA–IVD show the results of melatonin administration in the third cycle (November, 1984). These figures also show an anovulatory cycle following melatonin injection.

The data show three cycles wherein the administration of melatonin resulted in a suppression of the patient's normal pre-ovulatory surge of LH. The data also illustrates that there was a marginal suppression of FSH and pre-ovulatory estradiol and a significant reduction in progestrone levels. The LH supression is a sufficient indication that the patient did not ovulate in any of the three months in which melatonin was administered.

EXAMPLE II

The concentrations of LH, FSH, progestrone and estradiol in a patient's plasma were measured daily throughout three of the patient's menstrual cycles. The average concentration of each hormone for each day of the cycle was determined. The average concentration of the patient's LH peak was 295 ng/ml and the average of her FSH peak was 410 ng/ml. Her average progestrone level at the peak of the leuteal phase of her cycle was 14.5 ng/ml, and the average concentration of her estradiol peak was 0.6 ng/ml. The patient's peak in LH occurred on the fifteenth day of her cycle.

The patient was given an intravenous injection of 500 mg melatonin in a glucose in saline solution on each of days 7 through 12 of her cycle. The concentration of the four hormones in her plasma was measured throughout this cycle as before. The administration of melatonin was found to affect the hormone concentrations as follows:

peak PHC LH 110 ng/ml
FSH 295 ng/ml
estradiol 0.4 ng/ml
progestrone 0.3 ng/ml

These data indicate that the patient did not ovulate during this cycle; studies have shown that a peak of LH concentration of at least 250 ng/ml is necessary for ovulation.

EXAMPLE III

A woman having a normal menstrual cycle of 28 days with 3–5 days of moderate menstrual bleeding ($\pm 50$ ml. blood loss) was given intravenous injections of 350 mg melatonin in a glucose in saline solution for seven consecutive days, beginning on day 8 of her cycle. On days 14–28 of her cycle she was administered orally 0.75 mg norethindrone per day. The concentration of LH, FSH, progestrone and estradiol in her blood was measured daily throughout her cycle. She did not ovulate during this cycle (peak PHC LH was 115 ng/ml). She had a minimal menstrual blood loss ($\pm 15$ ml).

EXAMPLE IV

A woman having a normal menstrual cycle of 30 days (12th day ovulator) was given intravenous injections of 200 mg melatonin in a glucose in saline solution on each of days 7–10 of her cycle. She did not ovulate in this cycle, although the level of LH in her blood was found to be not uniformly suppressed but rather erratic with levels between 50 ng/ml and 180 ng/ml during the cycle. Her FSH PHC during this cycle was normal for her, her progesterone PHC was somewhat depressed, and her estradiol PHC throughout the cycle was normal.

EXAMPLE V

In an ongoing study, four women are taking melatonin in gelatin capsules. The melatonin is being administered in daily doses ranging from 30 mg. to 1000 mg. A preliminary evaluation indicates a satisfactory uptake of the melatonin from the gastrointestinal tract without negative side effects (such as diarrhea or nausea).

I claim:

1. A method of effecting contraception which comprises the administration, on a cyclic schedule, of melatonin in a series of daily doses to a human female of childbearing years at dose levels sufficient to prevent ovulation.

2. The method of claim 1 wherein the daily dosage level of melatonin ranges from about 2 mg to about 1000 mg per 70 kg body weight of the female.

3. The method of claim 2 wherein the daily dosage level is from about 30 mg to about 500 mg per 70 kg body weight.

4. The method of claim 1 which comprises administering melatonin daily for about 4–7 days, followed by about 21–26 days without melatonin administration.

5. The method of claim 4 wherein the daily dosage level of melatonin ranges from about 2 mg to about 100 mg per 70 kg body weight of the female.

6. The method of claim 5 wherein the daily dosage level of melatonin ranges from about 30 mg to about 500 mg per 70 kg body weight.

7. A method of effecting contraception which comprises the administration, on a cyclic schedule, of a combination of melatonin and a progestogen in a series of daily doses to a human female of child-bearing years at dose levels sufficient to prevent ovulation.

8. The method of claim 7 which comprises administering daily for about 21 days a combination of melatonin and a progestogen, followed by administering melatonin daily for about seven days but no progestogen.

9. The method of claim 7 which comprises administering daily for about 21 days a combination of melatonin and a progestogen followed by about 7 days without melatonin or progestogen administration.

10. The method of claim 7 which comprises administering melatonin daily for about 5–14 days, followed by administering daily a progestogen for about 7–14 days, for a total period of administration of about 21 days, followed by about 7 days without melatonin or progestogen administration.

11. The method of claim 7 which comprises administering a placebo daily for about 5 days, administering melatonin for about the next 3–7 days, and then administering a progestogen for about the next 9–13 days, for a total period of administration of about 21 days, followed by about 7 days in which no melatonin or progestogen is administered.

12. The method of claim 7 which comprises administering a progestogen for about 21–28 days and concurrently administering melatonin for about 1–7 days preceding the human female's normal day of ovulation.

13. The method of claim 7 wherein the progestogen is selected from the group consisting of norethindrone, norgestrel, chlormadinone-acetate, norethynodrel, medroxyprogesterone acetate, megestrol acetate lynestrenol, quingestrone, norethindrone acetate, ethynodiol acetate, levonorgestrel and dimethisterone.

14. The method of claim 7 wherein the dosage level of melatonin is from about 2 mg to about 1000 mg per 70 kg body weight on each day of administration and the dosage level of the progestogen is from about 7.5 micrograms to about 2500 mg per 70 kg body weight on each day of administration.

15. The method of claim 14, wherein the dosage level of progestogen is from about 7.5 micrograms to about 600 micrograms per 70 kg body weight on each day of administration.

16. The method of claim 14 wherein the progestogen is norethindrone or norgestrel.

17. The method of claim 14 wherein the estrogen is mestranol or ethinyl estradiol.

18. A method of effecting contraception which comprises the administration, on a cyclic schedule, of a combination of melatonin and an estrogen in a series of daily doses to a human female of child bearing years at dosage levels sufficient to prevent ovulation.

19. The method of claim 18 wherein the dosage level of melatonin is from about 2 mg to about 1000 mg per 70 kg of body weight on each day of administration and the dosage level of estrogen is from about 2 micrograms to about 1000 micrograms per 70 kg of body weight on each day of administration.

20. The method of claim 18 wherein the dosage level of melatonin is from about 30 mg to about 500 mg per 70 kg of body weight on each day of administration and the dosage level of estrogen is from about 10 micrograms to about 50 micrograms per 70 kg of body weight on each day of administration.

21. A method of effecting contraception which comprises the administration, on a cyclic schedule, of a combination of melatonin, a progestogen and an estrogen in a series of daily doses to a human female of child bearing years at a dosage level sufficient to prevent ovulation.

22. The method of claim 21 which comprises administering an estrogen for about 5–13 days, followed by the administration of melatonin for about 1–7 days prior to the female's normal day of ovulation, followed by the daily administration of progestogen for a total period of administration of about 21 days.

23. The method of claim 21 wherein the dosage level of melatonin is from about 2 mg to about 1000 mg per 70 kg body weight on each day of administration, the level of progestogen is from about 7.5 micrograms to about 2500 micrograms per 70 kg of body weight on each day of administration, and the dosage level of estrogen is from about 2 mg to about 100 micrograms per 70 kg of body weight on each day of administration.

24. The method of claim 18 or 21 wherein the estrogen is selected from the group consisting of ethinyl estradiol, mestranol, estradiol, estrone, estriol, diethylstilbestrol, quinestradiol and estrone sulfate.

25. The method of claim 1, 7, 18, 21, or 4 wherein the method of administration is oral.

26. The method of claim 1, 7, 18, 21, or 4 wherein the method of administration is by intravenous injection in a physiologically suitable carrier.

27. The method of claim 1, 7, 18, 21, or 4 wherein the method of administration is by implant.

28. A composition for effecting contraception in a human female of child-bearing age which comprises a contraceptively effective combination of melatonin and a progestogen.

29. A composition for effecting contraception in a human female of child-bearing age which comprises a contraceptively effective combination of melatonin and an estrogen.

30. A composition for effecting contraception in a human female of child-bearing age which comprises a contraceptively effective combination of melatonin, a progestogen and an estrogen.

31. The composition of claim 28 or 30 wherein the progestogen is selected from the group consisting of norethindrone, norgestrel, chlormadinone-acetate, norethynodrel, medroxyprogesterone acetate, megestrol acetate, lynestrenol, quingestrone, norethindrone acetate, ethynodiol acetate, levonorgestrel and dimethisterone.

32. The composition of claim 29 or 30 wherein the estrogen is selected from the group consisting of ethinyl estradiol, mestranol, estradiol, estrone, estriol, diethylstilbestrol, quinestradiol and estrone sulfate.

33. A method of effecting contraception which comprises the administration to a human female of child-bearing years of melatonin in 1 to about 5 post-coital daily dosages at a dosage level of about 1 g. to about 20 g. on each day of administration, administration being completed within about 5 days of coitus.

34. The method of claim 33, which comprises 1 to about 5 daily dosages at a dosage level of from about 5 g. to about 10 g. on each day of administration.

35. A method of effecting contraception which comprises the administration to a human female of child-bearing years of a combination of melatonin and a progestogen in about 1 to about 5 post-coital daily dosages, wherein the dosage level of melatonin is from about 1 g. to about 20 g. on each day of administration and the dosage level of progestogen is from about 10 mg. to about 20 mg. on each day of administration, administration being completed within about 5 days of coitus.

36. A method of effecting contraception which comprises the administration to a human female of child-bearing years of a combination of melatonin and an estrogen in 1 to about 5 post-coital daily dosages, wherein the dosage level of melatonin is from about 1 g. to about 20 g. on each day of administration and the dosage level of estrogen is from about 2.5 mg. to about 25 mg. on each day of administration, administration being completed within about 5 days of coitus.

* * * * *